United States Patent [19]

Luscombe et al.

[11] Patent Number: 5,358,510
[45] Date of Patent: Oct. 25, 1994

[54] TWO PART SURGICAL FASTENER

[75] Inventors: Brian H. Luscombe, Somerset; Izi Bruker, Flemington; Leslie Hamilton, Ringoes; Thu A. Le, Edison, all of N.J.

[73] Assignee: Ethicon, Inc., Somerville, N.J.

[21] Appl. No.: 9,157

[22] Filed: Jan. 26, 1993

[51] Int. Cl.$^5$ ............................................. A61B 17/00
[52] U.S. Cl. .................................. 606/220; 606/219; 606/151
[58] Field of Search .................. 606/219, 220, 151; 227/901, 902

[56] References Cited

U.S. PATENT DOCUMENTS

| | | |
|---|---|---|
| 4,060,089 | 11/1977 | Noiles . |
| 4,402,445 | 9/1983 | Green . |
| 4,506,670 | 3/1985 | Crossley . |
| 4,506,671 | 3/1985 | Green . |
| 4,513,746 | 4/1985 | Aranyi et al. . |
| 4,610,250 | 9/1986 | Green . |
| 4,667,674 | 5/1987 | Korthoff et al. ................... 606/220 |
| 4,724,839 | 2/1988 | Bedi et al. ........................... 606/220 |
| 4,890,613 | 1/1990 | Golden et al. ...................... 606/220 |
| 4,932,960 | 6/1990 | Green et al. . |
| 4,994,073 | 2/1991 | Green . |
| 5,089,009 | 2/1992 | Green ................................. 606/220 |

Primary Examiner—Stephen C. Pellegrino
Assistant Examiner—Gary Jackson
Attorney, Agent, or Firm—Paul A. Coletti

[57] ABSTRACT

A method of tissue compression is disclosed herein where the device to cause such compression is composed of a fastener bar and receiver. The device has the capability to self-adjust to tissues of varying thicknesses to cause hemostasis. This tissue gap variability allows for compression of regions of tissue where thick and thin tissue are both present. This variability also enables the same device to be used on a wide variety of tissues of different thicknesses. The tissue fastener bar of this invention contains a series of cut-out portions which distribute the compressive forces along the device in an alternating, staggered manner. The receiver is of a generally U-shaped configuration with the fastener bar being contained at least partially within the U-shape. Compression occurs between the side walls of the receiver and the fastener bar and variability in gap is accomplished by flexure of the side walls of the receiver. Varying side wall flexure is enhanced by cut-out portions in the receiver which allow each segment to flex somewhat independently. A number of options also exist for configuration of the fastener bar and/or receiver with the same basic method of compression being unchanged.

35 Claims, 9 Drawing Sheets

TWO PART SURGICAL FASTENER

FIELD OF THE INVENTION

This invention relates generally to surgical fasteners. More specifically, this invention relates to two part surgical fasteners wherein tissue may be joined between the fastener portion and a receiver portion. Most specifically, this invention relates to two part surgical fasteners wherein the receiver, which holds the fastener portion, enables the tissue to be placed into compression between the fastener and receiver.

BACKGROUND OF THE INVENTION

Surgical fasteners of two part construction are quite well-known in the art. Typically, these surgical fasteners which contain two parts are formed from one or more absorbable materials. The fastener itself contains a tissue piercing portion, i.e., a staple or fastener, and a receiving portion for the staple or fastener. The tissue to be joined may be generally two layers of tissue which are held between the fastener and receiver or may be tissue to be ligated. For cases where ligation occurs, it is generally the objective of the fastener to generate a compressive force on the tissue, which will prevent the flow of blood through the tissue. The absorbable nature of the fastener allows the fastener to be absorbed into the body after the separated tissue has adhered, so that there are no extraneous materials contained in the body after healing.

Yet, for all the tissue fasteners which are formed from a two piece construction, it has been observed that generally these fasteners maintain the tissue so that it is compressed between the fastener and the receiver in a fixed gap. That is, a portion of the tissue forms a layer which is below the fastener layer and above the receiver layer. The tissue contained between the fastener and receiver therefore undergoes compression due to the fixed gap which is present between the fastener and receiver and the resilient nature of the material that is being compressed. When traditional fixed-gap fasteners have been applied to tissues, this compressive force can significantly decrease over time due to the visco-elastic nature of the tissue. This can potentially lead to postoperative bleeding of the tissue which is not desirable. Additionally, the tissue will not be adequately compressed in traditional fastener/receivers if the fastener/receiver does not have the proper gap size for the type of tissue in question.

It is perceived that it is desirable to have tissue compression at a number of various places along the tissue which is to be ligated or joined. In traditional fastener/receiver systems this is accomplished by an alternating staggered line of individual fasteners with one or more receivers. This method of compression can be effective because it allows for capillary flow of blood at the fastener location which prevents necrosis of the tissue. However, it also requires a plurality of fasteners, each of which must penetrate the tissue. It has been observed that this multiplicity of penetrations can lead to localized bleeding at the locations of tissue penetration. The multiplicity of fasteners is also undesirable from a manufacturing viewpoint due to the number as well as size of the components involved. It is therefore desirable to create an alternative method for tissue compression which minimizes the number of penetrating fasteners.

Also, with such fasteners made from absorbable products, there has only been one way in which to adjust the gap or spacing between the tissue fastener and the staple receiver. This occurs via a ratcheting mechanism placed on the tissue piercing prongs of the fastener and creates a fixed gap between bottom of staple and top of receiver. When the piercing prongs are engaged in holes formed on the receiver, the ratcheting mechanism enables the device to be gradually closed to a varying thickness. Therefore, the final gap is reliant upon the instrument causing the fastener to ratchet to a determined position. The complexity associated with this increases the cost of the instrument and makes reliable ratcheting of the fasteners difficult, if not impossible. To simplify the instrument it would be desirable for the fastener to have the capacity to adjust automatically to the tissue.

By having the self-adjustment determined by the fastener and not the instrument, compression of adjacent tissues which are very different in thickness can be accomplished with a single self-adjusting device as opposed to two devices with different gap heights. In addition, the compressive force can be maintained even when the tissue loses its resiliency over time. Thus optimal tissue compression can be maintained by having the compression adjusted by the device itself, and not the instrument.

SUMMARY OF THE INVENTION

Accordingly, it is an object of the invention to provide a tissue staple fastener useful in combination with a receiver wherein the gap between the two components, which causes compression of the tissue, is capable of self-adjusting to the tissue being compressed, i.e. variable gap.

It is another object of the invention to provide a staple fastener useful in conjunction with a receiver wherein this variability in gap between the staple fastener and receiver is capable of varying along the length of the fastener so that regions of tissue with thick and thin components may be compressed simultaneously with the same tissue fastening device.

It is yet another object of the invention to form a tissue fastener which is able to be self-aligning so that it is always securely seated within the receiver.

It is yet another object of the invention to provide a tissue fastener wherein due to the configuration of the fastener and receiver, there is not a need for the fastener to be entirely placed within a single receiver, It is yet another object of this invention to accomplish fastening with a minimum number of penetration points into tissue; ideally, this should be accomplished in a self-adjusting fastener-receiver combination.

Finally, it is an object of the invention to provide a staple receiver wherein a tip shield guards the tip of the fastener after it is engaged in the hole of the receiver, so that the shield itself may protect the prong from piercing any tissue other than that tissue which the surgeon desires to pierce.

These and other objects of the invention are described in a combination fastener and receiver. The staple receiver contains a pair of generally parallel walls capable of flexing about the joined tissue and the fastener in a friction fit. The walls are separated by a base which is generally perpendicular to the walls. The fastener of this invention contains a tissue compressing bar which engages the walls and contains at least one tissue piercing prong which is generally placed perpendicular to the tissue compressing bar. Thus, tissue can be placed between the tissue compressing bar and the tissue compressing walls so that the gap between the walls holding the tissue can be varied to effect healing on both sides of the walls.

There is an option for the receiver walls to have a varying thickness. By varying the thickness and geometry of the side walls and/or the material of the receiver, the optimal compressive forces can be generated at varying degrees of flexure in the receiver walls and at varying locations along the fastener. The geometry of the side walls can also be modified to mate with varying geometric modifications to the fastener.

The tissue fastener of this invention also contains a series of cut-out portions which increase the adjustability of the device. These cut-outs allow the receiver walls to flex somewhat independent of one another from segment to segment. This improves the compression of the tissue and allows for compression of thicker tissues immediately adjacent to thinner tissues.

Additionally, it is not necessary for one fastener to be contained completely within a single receiver or vice versa. One long fastener may be used in conjunction with several shorter receivers or vice versa. When there is one or more fasteners engaging two or more receivers or vice versa, fasteners and receivers may be overlapped such that the fastener(s) engages a portion of one receiver as well as a portion of another adjacent receiver. Thus, given the new method of compression described, a number of various fastener/receiver configurations are possible.

It will be more readily apparent to the reader to derive the essence of this invention to the attached drawings taken in connection with the Detailed Description of the Invention.

DETAILED DESCRIPTION OF THE INVENTION

Figure 1:
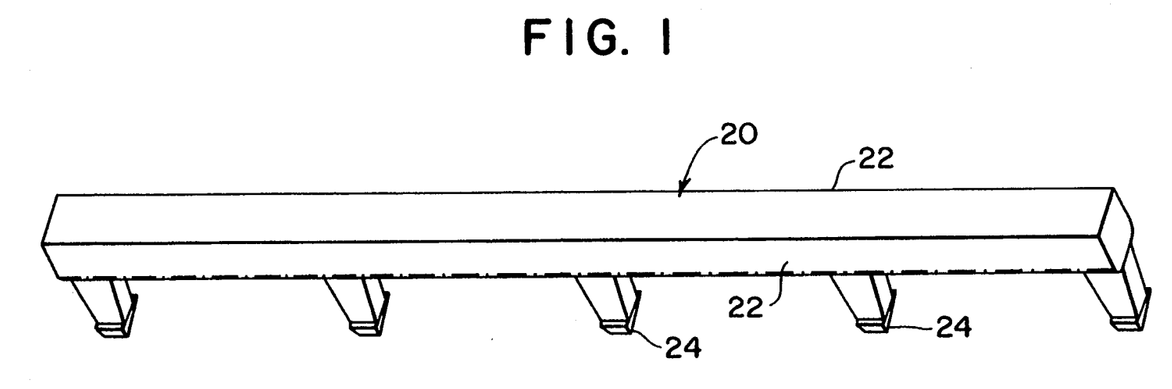
FIG. 1 is a perspective view of a multi-prong staple bar of the invention.
Figure 2:
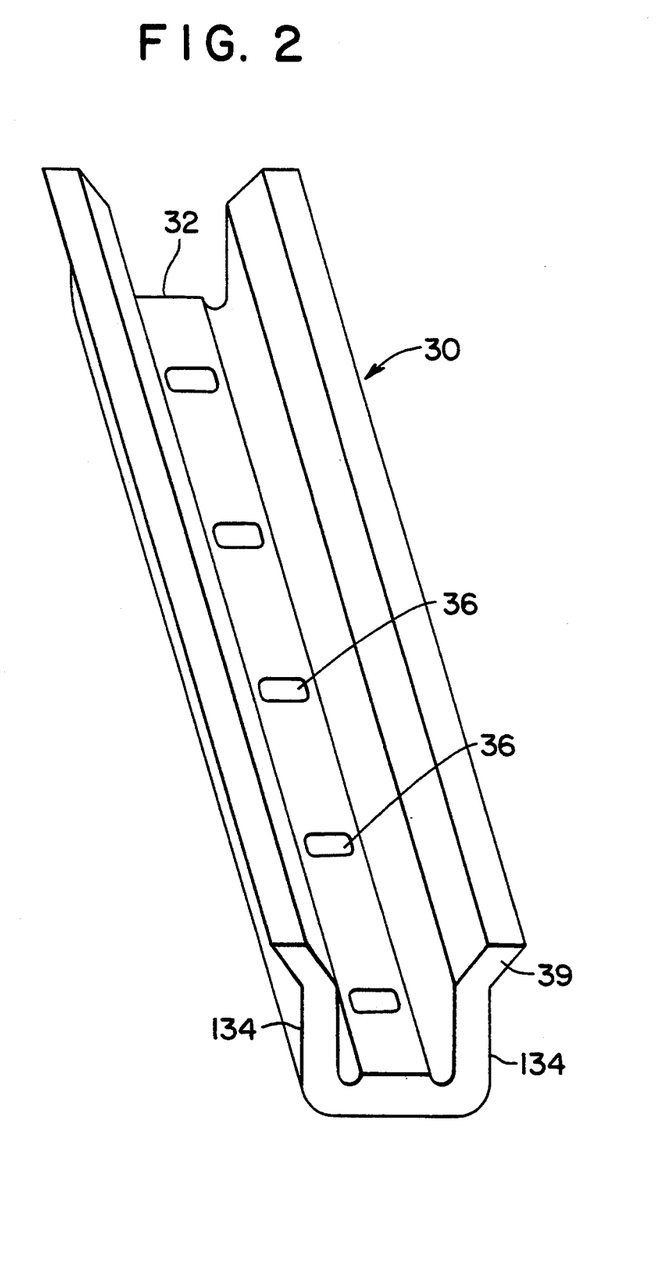
FIG. 2 is a perspective view of a staple receiver of the present invention.
Figure 3:
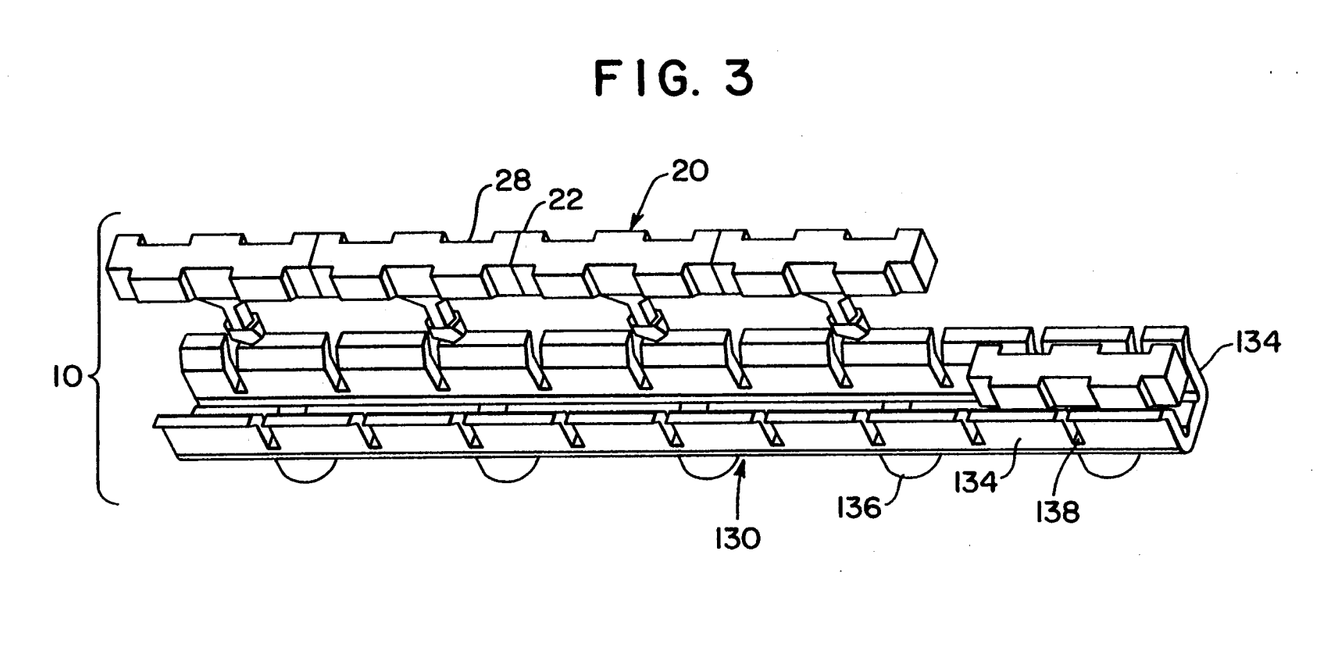
FIG. 3 is a perspective view of a series of single prong fasteners placed within a long staple receiver of the present invention.

As seen in FIGS. 1, 2 and 3, the current stapling configuration 10 of this invention comprises a stapling fastener bar 20 which contains at least one or possibly a plurality of staple prongs 24. These prongs 24 are capable of piercing tissue. The entire fastener is formed from one or more absorbable materials, such as polymeric bioabsorbable materials, so that it can be absorbed into the bloodstream. The staple is made from a material with a modulus of elasticity sufficiently high to allow the prongs to penetrate tissue, while the receiver is made of a material with a lower modulus of elasticity and greater flexibility than the staple. This staple bar may contain cut-out portions 28 on its walls 22 as further seen in FIG. 3. These cut-out portions will be later described.

Figure 4:
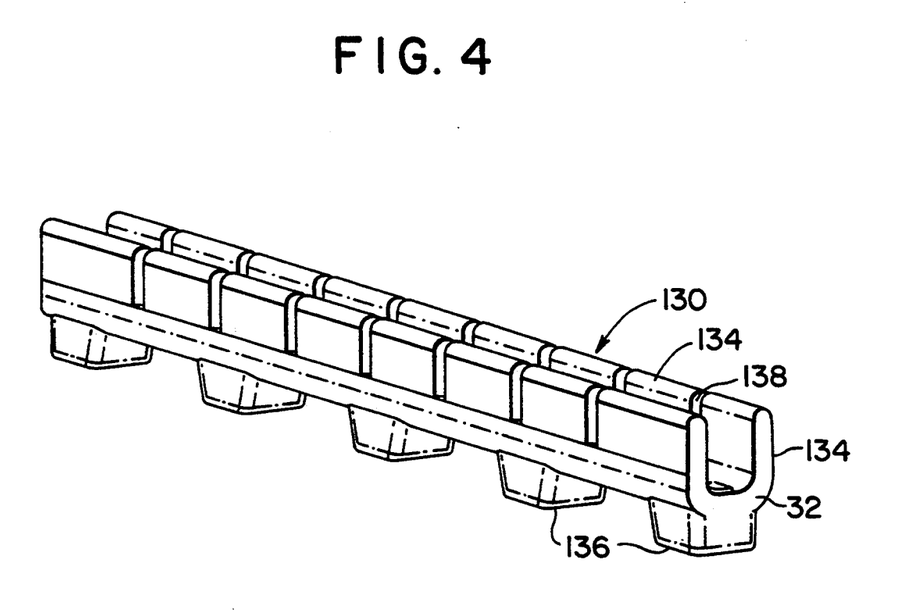
FIG. 4 is a staple receiver which contains tip shields as described by the present invention.
Figure 5:
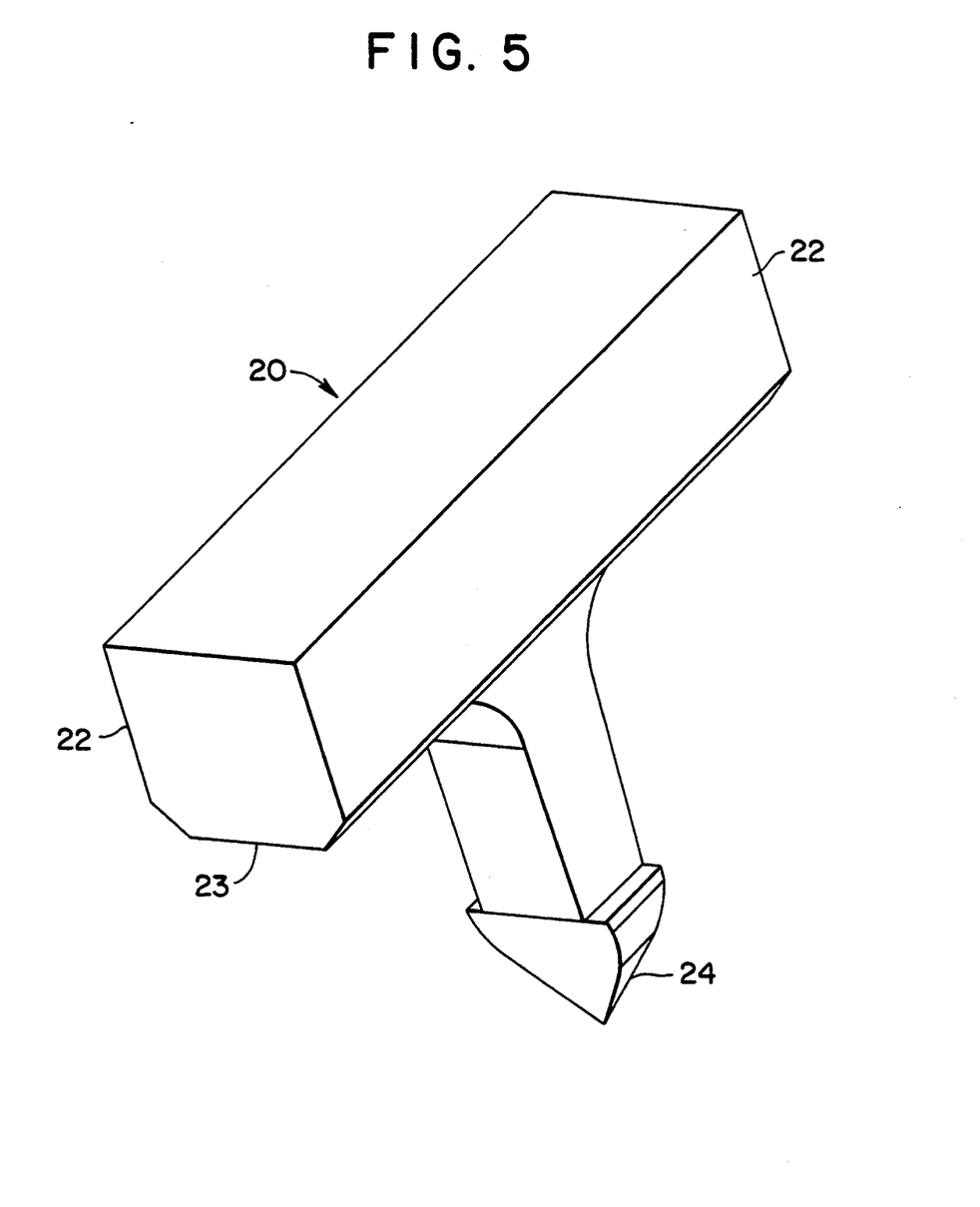
FIG. 5 is a perspective view of a single tissue fastener of the invention.

The stapling bar 20 of these Figures are useful in combination with a receiver 30, 130, 230, and 330 as described in FIGS. 2, 3, 4, 6, 7 and 8. A typical receiver 30 contains a base section 32 which separates a pair of generally parallel walls 134. The parallel walls 134 may have placed strategically along their length a series of slots 138 as contained in receiver 130 as seen in FIGS. 3 and 4. The base section 32 contains a series of holes 36 as seen in FIG. 2. These holes 36 may each contain a tip shield 136 as seen in FIG. 3.

The utility of these configurations is apparent upon further examination of the combination stapling bar 20 and any of the described receivers. The sides 22 of the bar 20 engage the walls of a respective receiver 30, 130. When tissue is contained therein, this causes the tissue to be compressed between the sides of the bar 20 and the walls 34, 134 of the respective receivers 30, 130.

As seen from the various configurations of the Figures, the current invention may be useful with a number of various options. First, as seen in FIG. 3 and as previously described, there can be contained cut-out portions 28 on the wall 22 of the fastener 20. These generally parallelepiped-shaped cut-out portions 28 are effective to provide a relief for the compression of the tissue. In this fashion, the receiver 30 compressing tissue within walls 34 and gap G, will not cause the tissue to necrose. Thus, stability of the tissue is retained while healing is still effective. The alternate staggering of compression also allows for microvascular circulation of the tissue, maintaining healthy tissue during healing.

Figure 6:
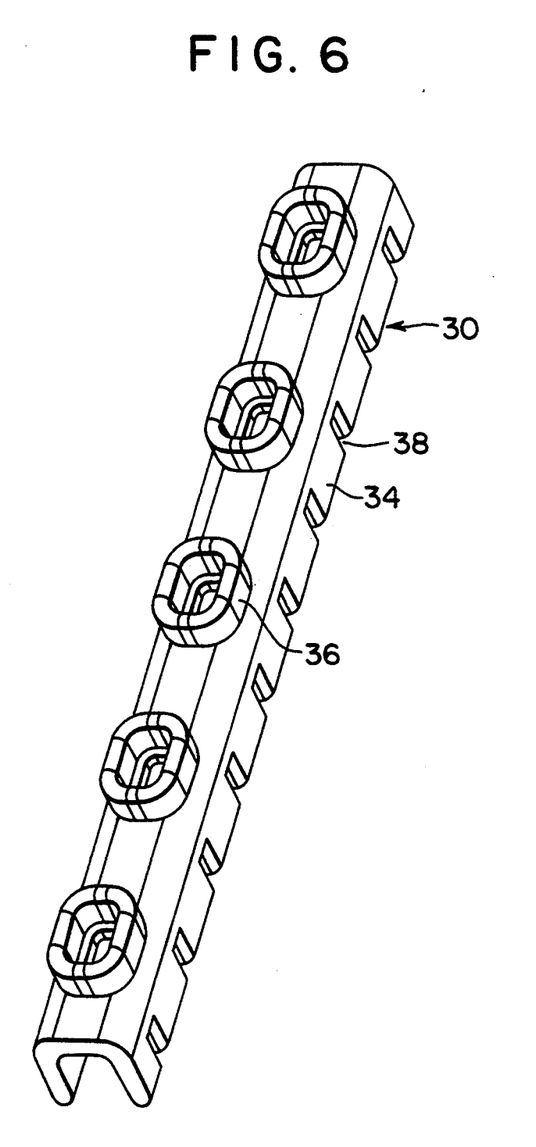
FIG. 6 is a lower perspective view of fastener of FIG. 4 which shows the tip shields of the present invention.

In a similar fashion as contained in FIGS. 3, 4 and 6, there may be contained relief slots 138 within the receiver walls 134. These relief slots 138 operate in very much the same fashion as cut-out portions 28. That is, the walls 22 of the staple bar 20 and the tissue contained therein cause the receiver walls 134 to expand. Thus, the relief provided by the slots 134 allows for the prevention of necrosis of the tissue.

As can be further seen from FIG. 2, for instance, there is a self-alignment feature very readily provided by this design. The walls 34 of the receiver 30 may be used such that they contain aligning flanges 39. These flanges 39 are angularly spaced from the walls 32 and cause the staple bars 20 to be aligned centrally therein when placed into the receiver 30. This alignment feature is useful when applying such a receiver endoscopically. That is, this alignment feature allows for a much wider tolerance of the bars 20 within receiver 30, for ease of use during an endoscopic procedure. Also, this configuration enables the user to position the staple bar 20 so that it is in an alternate configuration, it need not be placed at a strictly perpendicular 90° angle to the base 32 of receiver 30.

Figure 7:
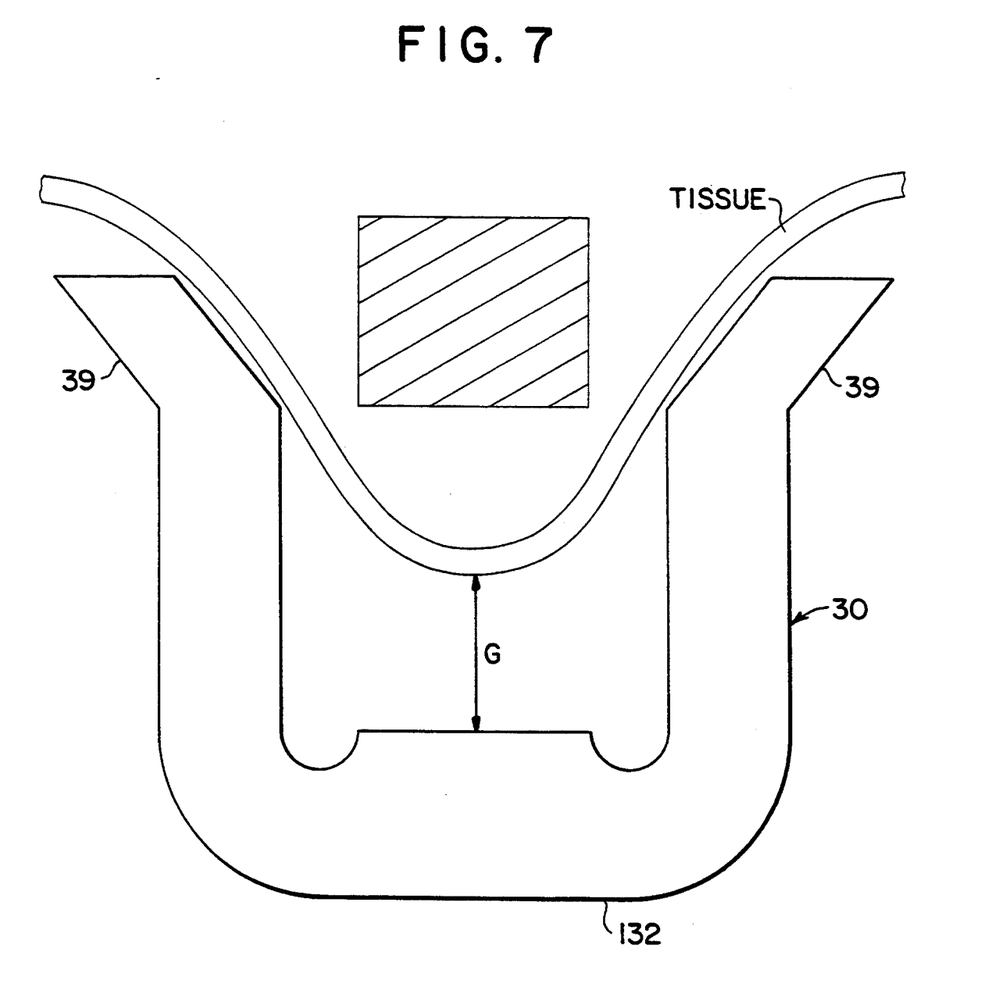
FIG. 7 and 7a are cross-sectional views showing emplacement of the fastener within the receiver of this invention.
Figure 7A:
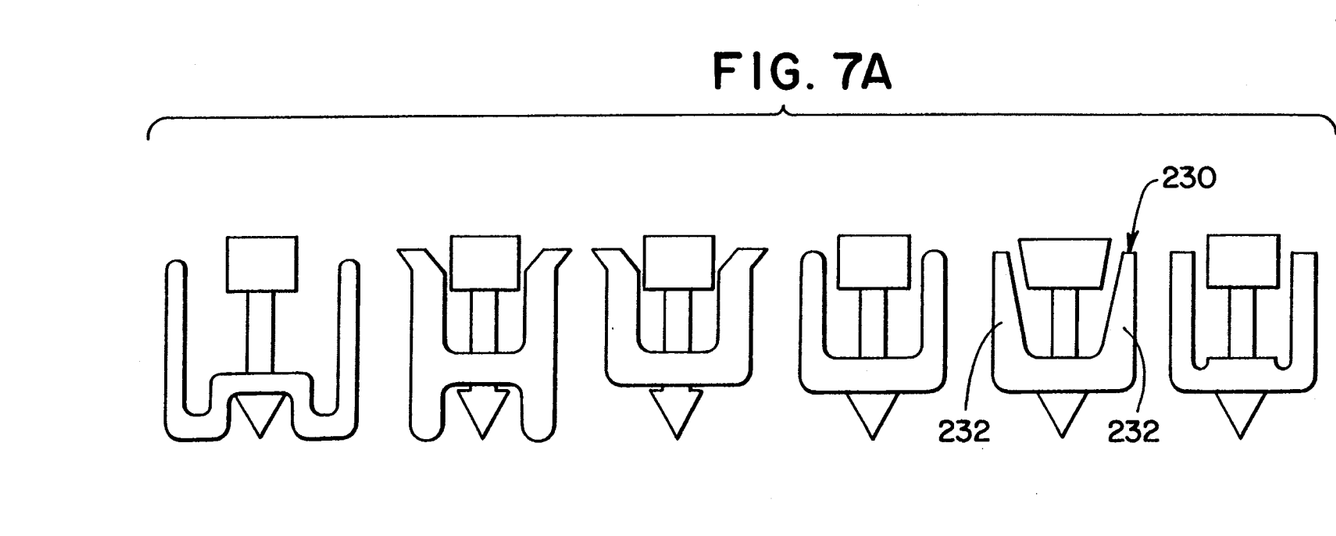
Figure 8:
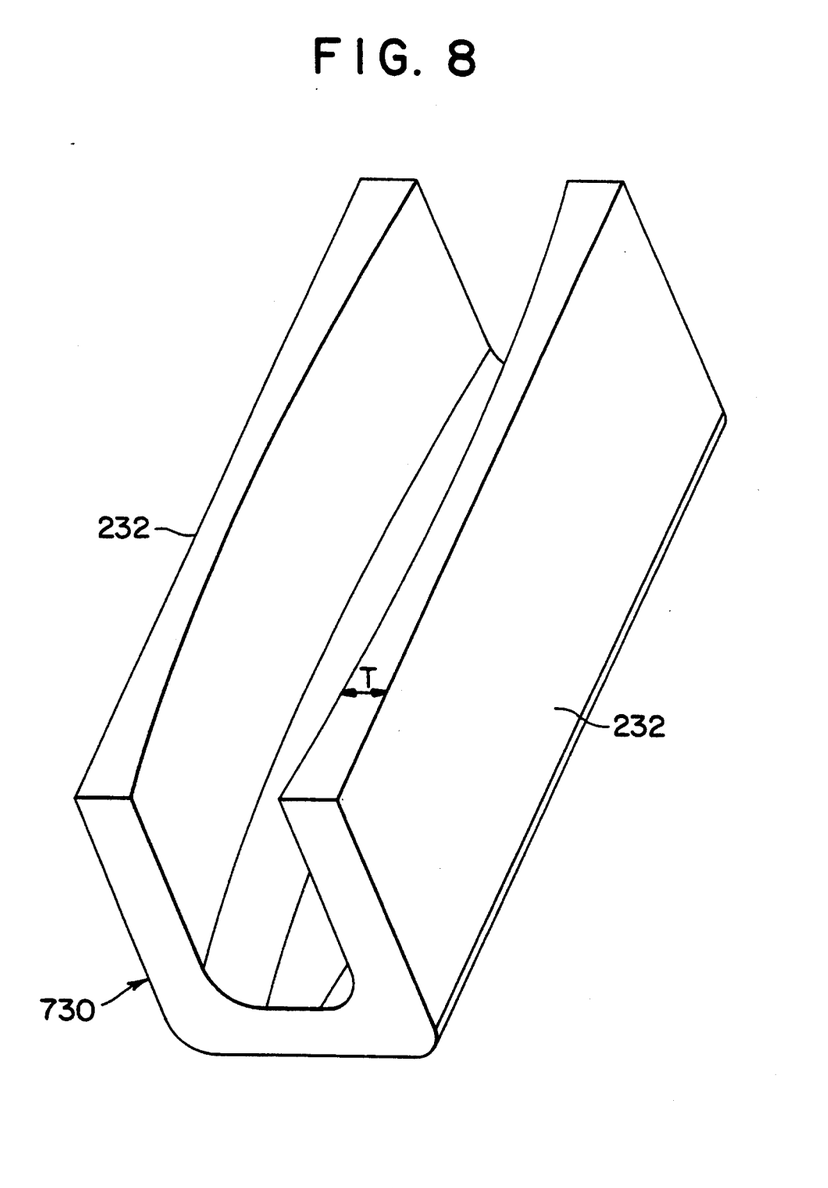
FIG. 8 is a perspective of an alternate receiver with varying wall thickness as described by the present invention.

As further seen in FIGS. 7a and 8, there is described by this invention a series of adjustability capabilities. That is, as seen in FIG. 8, there is contained a receiver 730 with varying wall thickness T in the receiver walls 232. This varying wall thickness T changes the stiffness of the wall which has the effect of changing the compressive force generated on the tissue as a function of the distance along the receiver length. This option maybe applied to a receiver without cut outs as seen in FIG. 8, or may be applied to the portions of the side walls 134 created by the cut outs 138.

Further, as seen in FIG. 7a, the staple bar 20 may be configured within a trapezoidally shaped cross section. This may be useful either with uniform wall thickness or the variable wall thickness as described in FIG. 8. This trapezoidally shaped staple bar causes the same function as the walls 232 of the receiver in FIG. 8. Of course, other geometries are useful to accomplish this healing.

Ideally, the prongs 24 of the receiver may be placed within holes 36 contained in the receiver base 32. This causes a near perfect alignment of the bar 20 in the receiver 30. Nonetheless, while it may be desirable to place the prongs 24 of the bar 20 within the receiver holes 36 in the base 32, it may also be desirable to protect the exterior of the base 32 from the protruding prongs 24. Therefore, the base 32 of FIG. 4, for instance, is provided with a tip shield 136 on the exterior of the portion of the receiver 130. These tip shields 136 cover any protrusion of the prong 24 from the base 132. In this fashion, tissue is protected after joining of the prongs 24 in the holes 36 of the base 132. It is to be realized that shields 136 can also be used to locate the receiver 130 in a cartridge via a friction fit.

Finally, it is to be realized that the staple of this configuration allows for various configurations of staples and receivers. As seen in many of the figures, it is not necessary for a particular fastener bar 20 to be the same length as a particular receiver 30. In addition, it is not necessary for a particular receiver 30 to be longer than a particular fastener bar 20. Any number of combinations are possible. Therefore, a fastener bar 20 may be placed within a receiver so that other prongs 24 fit with other receivers 30 placed alongside receiver 30. Alternately, an entire fastener bar 20 may be placed within a receiver 30 while the ends of the receiver 30 contains prongs 24 from other bars. Or, as may be considered more conventional, the receiver 30 may be emplaced to identically fit the length of a fastener bar 20.

It is therefore realized that what is to be understood from the foregoing invention is the claims and the equivalents contained therein.

We claim:

1. A surgical fasteners used to pierce tissue, said fasteners comprising a tissue compressing bar and at least one tissue piercing prong extending therefrom, said prong having a height, and a receiver adapted to receive said tissue compressing bar and said at least one prong, having a generally uniform width and a height, said receiver comprising:
   a pair of generally parallel walls adapted to receive said bar width therein with tissue compressed therebetween, said walls having a height, and said walls separated by and connected to a base generally perpendicular to said walls.

2. The receiver of claim 1 wherein said walls have a generally uniform thickness.

3. The receiver of claim 1 wherein said walls have a generally varying thickness.

4. The receiver of claim 1 wherein said base has a tip shield assembly comprising a hole and a shielding member surrounding said hole, said tip shield assembly protruding from said base.

5. The receiver of claim 1 wherein said walls contain lead-in flanges attached to said walls at an angular displacement from said walls, and said flanges serving to align said fasteners with said walls.

6. The receiver of claim 1 wherein said walls contain a series of slots therein; said slots dividing said walls into smaller sections such that adjacent ones of said sections may flex relative to one another.

7. The receiver of claim 1 wherein said receiver is formed from a polymeric bioabsorbable material.

8. A receiver for holding surgical fasteners used to pierce tissue, said fasteners comprising at least one tissue piercing prong having a height, and said prongs extending from a tissue compressing bar said receiver adapted to receive said tissue compressing bar and said at least one prong, said receiver having a generally uniform width and a height, said receiver comprising:
   a pair of generally parallel walls having a height and a width adapted to receive said bar width therein with tissue compressed therebetween, and said walls separated by and connected to a base generally perpendicular to said walls; and
   wherein said walls contain lead-in flanges attached to said walls at an angular displacement from said walls, and said flanges serving to align said fasteners with said walls.

9. The receiver of claim 8 wherein said receiver is sized to accept tissue between a bar of said fastener and said base.

10. The receiver of claim 8 wherein said walls have a generally uniform thickness.

11. The receiver of claim 8 wherein said walls have a generally varying thickness.

12. The receiver of claim 8 wherein said base has a tip shield assembly comprising a hole and a shielding member surrounding said hole, said tip shield assembly protruding from said base.

13. A surgical fastener comprising at least one tissue piercing prong connected to a bar, said bar having a length and a width separating a pair of sides, each of said sides having a series of cut-out portions placed along said sides, said cut-out portions being generally parallelepiped-shaped.

14. The fastener of claim 13 wherein said width is variable along said length.

15. The fastener of claim 13 wherein said bar cross section is generally trapezoidal.

16. In combination:
    a fastener comprising at least one tissue piercing prong and said prong extending from a tissue compressing bar having a generally uniform width and a height; and
    a receiver for holding said fastener, said receiver containing a pair of generally parallel walls having a height and a width adapted to receive said at least one prong and said bar width therein, and said walls separated by and connected to a base generally perpendicular to said walls.

17. The combination of claim 16 wherein said receiver is sized to accept tissue between a bar of said fastener and said base.

18. The combination of claim 17 wherein said walls contain a series of parallel slots therein; said slots dividing said walls into smaller sections such that adjacent ones of said sections may rotate relative to one another.

19. The combination of claim 16 wherein said walls have a generally uniform thickness.

20. The combination of claim 16 wherein said walls have a generally varying thickness.

21. The combination of claim 16 wherein said base has a tip shield assembly comprising a hole and a shielding member surrounding said hole, said tip shield assembly protruding from said base.

22. The combination of claim 16 wherein said walls contain lead-in flanges attached to said walls at an angular displacement from said walls, and said flanges serving to align said fasteners with said walls.

23. The combination of claim 16 wherein said bar has a generally trapezoidal cross section.

24. The combination of claim 16 wherein said bar width separates a pair of sides and each of said sides having a series of cut-out portions placed along said sides, said cut-out portions being generally parallelepiped-shaped.

25. The receiver of claim 18 wherein said receiver is formed from a polymeric bioabsorbable material.

26. In combination:
- a fastener comprising at least one tissue piercing prong and said prong extending from a tissue compressing bar having a generally uniform width and a height; and
- a receiver for holding said fastener, said receiver containing a pair of generally parallel walls having a height and a width adapted to receive said at least one prong and said bar width therein in a friction fit, and said walls separated by and connected to a base generally perpendicular to said walls; and
- wherein said walls contain lead-in flanges attached to said walls at an angular displacement from said walls, and said flanges serving to align said fasteners with said walls.

27. The combination of claim 26 wherein said receiver is sized to accept tissue between a bar of said fastener and said base.

28. The combination of claim 26 wherein said walls have a generally uniform thickness.

29. The combination of claim 26 wherein said walls have a generally varying thickness.

30. The combination of claim 26 wherein said base has a tip shield assembly comprising a hole and a shielding member surrounding said hole, said tip shield assembly protruding from said base.

31. The combination of claim 26 wherein said walls contain a series of parallel slots therein; said slots dividing said walls into smaller sections such that adjacent ones of said section may rotate relative to one another.

32. The combination of claim 26 wherein said bar has a generally trapezoidal cross section.

33. The combination of claim 26 wherein said bar width separates a pair of sides and each of said sides having a series of cut-out portions placed along said sides, said cut-out portions being generally parallelepiped-shaped.

34. In combination:
- a fastener comprising at least one tissue piercing prong and said prong extending from a tissue compressing bar having a generally uniform width and a height;
- a receiver for holding said fastener, said receiver containing a pair of generally parallel walls having a height and a width adapted to receive said at least one prong and said bar width therein in a friction fit, and said walls separated by and connected to a base generally perpendicular to said walls; and
- wherein said bar is configured so that at least a portion of said bar protrudes over and end of said receiver.

35. A method of closing tissue comprising: providing a fastener and receiver, said fastener comprising at least one tissue piercing prong having a height and a tissue compressing bar, and said receiver having a pair of walls capable of engaging said bar;
- placing tissue between said fastener and said receiver; and
- applying a compressive force to said tissue held within said bar and said receiver.

* * * * *